(12) United States Patent
Kuchler et al.

(10) Patent No.: US 10,034,348 B2
(45) Date of Patent: Jul. 24, 2018

(54) LIGHT-EMITTING APPARATUS

(71) Applicant: OSRAM GmbH, Munich (DE)

(72) Inventors: Thomas Kuchler, Munich (DE); Oskar Schallmoser, Ottobrunn (DE)

(73) Assignee: OSRAM GMBH, Munich (DE)

( * ) Notice: Subject to any disclaimer, the term of this patent is extended or adjusted under 35 U.S.C. 154(b) by 249 days.

(21) Appl. No.: 15/159,904

(22) Filed: May 20, 2016

(65) Prior Publication Data

US 2016/0341673 A1    Nov. 24, 2016

(30) Foreign Application Priority Data

May 21, 2015 (DE) .................. 10 2015 209 340

(51) Int. Cl.
*H05B 33/08* (2006.01)
*F21S 41/16* (2018.01)
(Continued)

(52) U.S. Cl.
CPC ............ *H05B 33/089* (2013.01); *F21S 41/16* (2018.01); *H05B 33/0851* (2013.01); *F21S 41/14* (2018.01); *F21V 3/00* (2013.01); *F21V 9/30* (2018.02); *F21W 2102/00* (2018.01); *F21W 2131/406* (2013.01); *F21Y 2115/30* (2016.08); *G01N 21/8851* (2013.01); *G01N 21/95* (2013.01)

(58) Field of Classification Search
CPC .... H05B 33/089; H05B 33/0851; F21S 41/16
See application file for complete search history.

(56) References Cited

U.S. PATENT DOCUMENTS 8,496,333 B2 * 7/2013 Wang ................. G02B 26/0833
                                                           353/84
2011/0043764 A1    2/2011 Narikawa
(Continued)

FOREIGN PATENT DOCUMENTS

CN    101995749 A    3/2011
CN    102042549 A    5/2011
(Continued)

OTHER PUBLICATIONS

Chinese Office Action based on application No. 201610221398.0 (6 pages and 7 pages of English translation) dated Jun. 26, 2017.
(Continued)

*Primary Examiner* — David Porta
*Assistant Examiner* — Mindy Vu
(74) *Attorney, Agent, or Firm* — Viering, Jentschura & Partner mbB (57) ABSTRACT

In various embodiments, a light-emitting apparatus is provided. The light-emitting apparatus includes at least one semiconductor light source configured to emit at least one primary light beam, a deflection device configured to deflect the at least one primary light beam onto respectively associated different positions on a phosphor body, at least one light detector configured to detect light that was emitted by the phosphor body, and an evaluation device. The evaluation device is configured to identify damage to the phosphor body on the basis of at least one measurement signal generated by the at least one light detector, and to correlate the at least one measurement signal with at least one position on the phosphor body.

18 Claims, 2 Drawing Sheets

(51) Int. Cl.
*F21V 3/00* (2015.01)
*F21W 131/406* (2006.01)
*G01N 21/88* (2006.01)
*G01N 21/95* (2006.01)
*F21Y 115/30* (2016.01)
*F21S 41/14* (2018.01)
*F21W 102/00* (2018.01)
*F21V 9/30* (2018.01)

(56) References Cited

U.S. PATENT DOCUMENTS

| | | |
|---|---|---|
| 2011/0084609 A1 | 4/2011 | Kawaguchi et al. |
| 2011/0261326 A1 | 10/2011 | Wang et al. |
| 2012/0050691 A1 | 3/2012 | Tsuda et al. |
| 2016/0187608 A1* | 6/2016 | Brown ............... G01M 11/37 356/73.1 |
| 2017/0240094 A1* | 8/2017 | Kunecke ............ B60Q 1/0023 |

FOREIGN PATENT DOCUMENTS

| | | |
|---|---|---|
| CN | 102235618 A | 11/2011 |
| CN | 102385227 A | 3/2012 |
| CN | 103994383 A | 8/2014 |
| DE | 102014202943 A1 | 8/2015 |
| EP | 2767751 A1 | 8/2014 |
| WO | 2014072226 A1 | 5/2014 |
| WO | 2015000006 A1 | 1/2015 |

OTHER PUBLICATIONS

German Search Report based on Application No. 10 2015 209 340.9(9 Pages) dated Dec. 3, 2015.

* cited by examiner

LIGHT-EMITTING APPARATUS

CROSS-REFERENCE TO RELATED APPLICATION

This application claims priority to German Patent Application Serial No. 10 2015 209 340.9, which was filed May 21, 2015, and is incorporated herein by reference in its entirety.

TECHNICAL FIELD

Various embodiments relate generally to a light-emitting apparatus, having at least one semiconductor light source for emitting at least one primary light beam, a deflection device for deflecting the at least one primary light beam onto respectively associated different positions on a phosphor body, and at least one light detector for detecting light that was emitted by the phosphor body. Various embodiments are applicable e.g. to projection apparatuses such as vehicle headlights, stage projectors etc.

BACKGROUND

Stationary LARP ("Laser Activated Remote Phosphor") systems are known, in which a wavelength-converting phosphor is illuminated across a large area by a stationary blue laser beam ("primary light beam") and in the process converts the laser light partially into yellow light ("secondary light"). The non-converted blue primary light and the converted yellow secondary light together give white mixed light. If the phosphor is damaged or even removed completely from the beam path, the primary light can exit the LARP system in greater proportions and, in addition, coherently. To prevent this, it is conventional to use two light detectors that are sensitive to the primary light or the secondary light and to deduce failure of the phosphor on the basis of the ratio of the strengths of their measurement signals. If failure is ascertained, the LARP system can be switched off ("safety switch-off") or a luminous flux of the primary light can be reduced until safety regulations are complied with ("emergency light operation"). However, this method may have the effect that minor damage to the phosphor is detectable only with difficulty, and a reaction to damage practically results in a malfunction of the LARP system.

WO 2015/000006 A1 discloses a vehicle headlight having at least one laser light source, the laser beam of which is deflected, via a micromirror that is pivotable about at least one axis, to a light-emitting surface having a light-conversion phosphor so as to generate at said light-emitting surface a light-emitting image in a scanning fashion, which can be projected onto a driving lane via an optics. In this headlight, at least one photosensor is positioned with respect to the light-emitting surface having the light-conversion phosphor such that it captures, in predetermined deflection orientations of the micromirror, a secondary laser beam emanating from the light-emitting surface and is adapted for emitting a signal.

SUMMARY

In various embodiments, a light-emitting apparatus is provided. The light-emitting apparatus includes at least one semiconductor light source configured to emit at least one primary light beam, a deflection device configured to deflect the at least one primary light beam onto respectively associated different positions on a phosphor body, at least one light detector configured to detect light that was emitted by the phosphor body, and an evaluation device. The evaluation device is configured to identify damage to the phosphor body on the basis of at least one measurement signal generated by the at least one light detector, and to correlate the at least one measurement signal with at least one position on the phosphor body.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

Various embodiments provide a light-emitting apparatus having at least one semiconductor light source and a phosphor body, which permits improved reaction to damage of the phosphor body.

Various embodiments provide a light-emitting apparatus, having at least one semiconductor light source for emitting at least one primary light beam, a deflection device for deflecting the at least one primary light beam onto respectively associated different positions on a phosphor body, at least one light detector for detecting light that was emitted by the phosphor body, and an evaluation device that is adapted for: (a) identifying damage to the phosphor body on the basis of at least one measurement signal generated by the at least one light detector; and (b) correlating the at least one measurement signal with at least one position on the phosphor body.

This light-emitting apparatus may have the effect that it can simply localize a site of damage on the phosphor body (that is to say enable better spatial resolution of a defect region on the phosphor body) and trigger, for example in dependence on a type and/or extent of the damage, a corresponding action. In various embodiments, it is thus possible to link cost-effective, because practically not spatially resolving light detection in a simple manner with locational information so as to be able to ascertain a site of damage of the phosphor body with a high degree of accuracy.

The at least one semiconductor light source may include at least one laser. The laser can be a diode laser. The at least one semiconductor light source can also have at least one light-emitting diode. The semiconductor light source emits e.g. blue primary light, e.g. having a wavelength of 440 nm, for example.

A diameter of the primary light beam is typically significantly smaller than a surface of the phosphor body that is to be illuminated by said primary light beam.

The deflection device can have at least one movable mirror. The at least one movable mirror can include at least one rotatable or pivotable mirror, but can, in addition or alternatively, also be displaceable. A rotatable mirror can assume a plurality of settings in the form of angular settings. The at least one mirror can be moved in steps or continuously so that it moves. The at least one mirror may be a resonantly operated or moved mirror, for example a MEMS ("Micro Electro-mechanical System") or a DMD ("Digital Mirror Device"). The deflection device can have, in addition to the at least one movable mirror, at least one further optical element, for example at least one lens.

In a further development, the at least one movable mirror is exactly one mirror, which permits particularly simple construction. Such a mirror is pivotable or rotatable e.g. about two mutually perpendicular rotation axes, for example about an x-axis and about a y-axis.

In another further development, the at least one movable mirror includes a plurality of movable mirrors. Said movable mirrors can redirect primary light beams for example in respectively different spatial directions, for example for a row-wise or column-wise structure of the light emission pattern. Specifically, in each case one rotatable mirror per rotation axis can be present, such as for example one rotatable mirror for the x-axis and one rotatable mirror for the y-axis that is connected downstream, or vice versa. Such mirrors can be implemented in a particularly simple manner.

Using the deflection device, it is thus possible for the at least one primary light beam to sweep over the phosphor body along tracks, or for a luminous spot generated by a primary light beam on the phosphor body to follow a track on the phosphor body. This can also be referred to as a "scanning" arrangement. The track can correspond for example to a row-wise or column-wise illumination or a Lissajous curve. The primary light beam does not need to be switched on continuously, however; it is possible for illuminated and non-illuminated phases to alternate to generate an image pattern. However, the at least one primary light beam or the at least one associated semiconductor light source can also be switched on such that it brings about uniform illumination of the phosphor body. In the case of illumination of the phosphor body by means of a closed figure (for example a Lissajous curve), the primary light beam can be switched on continuously, for example. In the case of a row-wise or column-wise illumination, it may also be switched on continuously except when it jumps back to the beginning of rows or columns. As opposed to a stationary, large-area illumination of the phosphor body, the track-type illumination of the phosphor body by the at least one primary light beam permits the detection of local damage in a simple manner. To illustrate a desired image pattern, that is to say an intensity pattern, on the phosphor body, the primary light sources can be operated in particular in a modulated fashion.

In a further development, the light-emitting apparatus is what is known as a "flying spot" apparatus, which uses the scanning method and in the process can generate an image pattern on the phosphor body by varying the at least one primary light beam, for example by switching it on and off and/or modulating the intensity.

In a further development, the phosphor body can be or is illuminated by means of exactly one primary light beam, which permits a particularly simple construction.

In another further development, the phosphor body can be or is illuminated by means of a plurality of disjointed primary light beams, which permits a particularly high luminous flux. The plurality of light beams is "disjointed" in particular in the sense that they do not or do not always strike the same point on the phosphor body. A plurality of disjointed primary light beams can also be guided via a common deflection device or via a plurality of deflection devices. The primary light beams can here be oriented such that they are parallel and/or not parallel with respect to one another.

The "illumination regions" of the phosphor body that can be illuminated by each of the plurality of disjointed primary light beams can be the same. For example, a specific partial region of the phosphor body can be successively illuminated by a plurality of primary light beams, typically with a time interval.

In another further development, the illumination regions that are associated with a plurality of disjointed primary light beams differ. They can overlap or not overlap or even be spatially disjointed.

A time period necessary to illuminate the phosphor body once completely, within the context of image information that is to be represented over the entire area, can be referred to as "image buildup time". The latter can have a repetition frequency of a few hundred hertz, for example 250 Hz. If the phosphor body undergoes row-wise scanning, the number of rows can be in particular up to a few hundred, for example 300. For an image refresh frequency of 250 Hz and a row number of 300, the result is, for example, an image buildup time of 13 µs per row.

The phosphor body has at least one phosphor that is suitable for converting incident primary light at least partially into secondary light having a different wavelength. If a plurality of phosphors is present, they can generate secondary light of mutually different wavelengths and/or generate the secondary light by primary light of a different wavelength. The wavelength of the secondary light can be longer (what is known as "down conversion") or shorter (what is known as "up conversion") than the wavelength of the primary light. By way of example, using a phosphor, blue primary light can be converted into green, yellow, orange or red secondary light. In the case of an only partial wavelength conversion, the phosphor body emits a mixture of secondary light (for example yellow) and unconverted primary light (for example blue) that can serve as the used light (for example white).

The phosphor body can be a (flat) phosphor platelet, for example in the form of a ceramic, for example composed of cerium-doped yttrium aluminum garnet (Ce:YAG). The phosphor body can also be a carrier—for example composed of sapphire—that is covered by a phosphor layer. The phosphor body can be planar at least at the surface that is to be irradiated by the primary light beams. The phosphor platelet can have a constant or varying thickness. By way of example, it can have a round or square edge contour.

Alternatively or additionally, the phosphor platelet can also be configured to be non-planar at least at the surface that is to be irradiated by the primary light beams, for example be curved or undulated.

The phosphor body can be an individual phosphor body that is produced in a contiguous fashion, which is also referred to as a unipartite phosphor body. Alternatively, the phosphor body can be made up of separately manufactured partial segments which are offset and/or rotated and/or inclined and/or tilted with respect to one another. The partial segments can be arranged on a common plane, but do not need to be.

These partial segments or partial phosphor bodies can have identical or different conversion properties (for example with respect to a degree of conversion, a phosphor that is used, etc.). The partial segments can directly adjoin one another and/or be physically apart.

The phosphor body can be present or used in a reflecting arrangement and/or in a transmitting arrangement. In the reflecting arrangement, the light that is used as the used light is that light emitted by the phosphor body which is emitted on that side of the phosphor body on which the primary light beams are also incident. In the transmitting arrangement, the light that is used as the used light is that light emitted by the phosphor body which is emitted on that side of the phosphor body that is remote with respect to the incident primary light beams. In various embodiments, both a reflecting and a transmitting arrangement can be implemented. Further optical elements, such as for example dichroic mirrors, can be implemented for increasing the efficiency especially in a transmitting arrangement.

A first optics in the form of a "primary optics", which individually shapes, e.g. collimates, the primary light beam(s) emitted by the at least one semiconductor light source can be connected downstream of the at least one semiconductor light source.

A second optics with at least one optical element can be arranged in the light path between the at least one semiconductor light source or—if present—the first primary optics and the deflection device. A third optics with at least one optical element can be arranged in the light path between the deflection device and the phosphor body. Optically connected downstream of the phosphor body can be a fourth optics with at least one optical element for beam-shaping the used light. The third optics and the fourth optics can have at least one common optical element, for example at least one optical element for focusing primary light beams onto the light-emitting body and for outputting the used light that is emitted by the phosphor body.

It is also possible for further optics or optical elements to be present.

In a further development, at least one photodetector or light detector is configured to detect only primary light—and thus no secondary light. Damage to the phosphor body can thus, for example, be identified on the basis of an intensity of the primary light that is noticeably too low or noticeably too high. The light detector can have or be, for example, a photodiode.

In another further development, at least one light detector is configured to detect only secondary light—and thus no primary light. Damage to the phosphor body can thus, for example, be identified on the basis of an intensity of the secondary light that is noticeably too low or noticeably too high.

In yet another further development, at least one light detector is configured to detect both primary light and secondary light. Damage to the phosphor body can thus, for example, be identified on the basis of an intensity of the mixed light that is noticeably too low or noticeably too high. At least one light detector can also be configured to detect damage to the phosphor body by way of a changed ratio of (e.g. normalized) primary light intensity to the intensity of the conversion light, thus for example a blue/yellow ratio.

In another further development, the at least one light detector is exactly one light detector, the field of vision of which includes e.g. the entire area of the phosphor body that can be illuminated. This permits a particularly simple and cost-effective construction. As a result, the entire region of the phosphor body that can be illuminated or irradiated by primary light radiation can be monitored using exactly one light detector.

In another further development, the at least one light detector includes a plurality of light detectors, the fields of vision of which include in each case the entire area of the phosphor body that can be illuminated and which are sensitive to different wavelength ranges, e.g. identify or detect either primary light or secondary light. Damage to the phosphor body can be particularly reliably determined. As a result, in each case the entire region of the phosphor body that can be irradiated can be monitored using a plurality of different light detectors.

In another further development, the at least one light detector has a plurality of light detectors, the fields of vision of which include different areas ("illumination regions") of the phosphor body that can be illuminated. These light detectors can be sensitive in particular to identical wavelength ranges, in particular to primary light and/or secondary light. Damage to the phosphor body can be determined in particularly high resolution and thus quickly and reliably by way of this further development. The fields of vision of the plurality of light detectors on the phosphor body can overlap or not overlap or be "disjointed". The overlapping arrangement may have the effect that non-detectable or "blind" regions of the region of the phosphor body that can be illuminated can be reliably excluded. The disjointed arrangement of the fields of vision may have the effect that damage can be uniquely associated with a detector and thus determination of the site of damage is facilitated. The disjointed arrangement of the fields of vision may be applied e.g. if it corresponds to a corresponding arrangement of disjointed illumination regions.

The correlation can be a time correlation, in particular between a time or time period of a measurement signal that is associated with a specific damage and a position of the at least one primary light beam on the phosphor body that corresponds to said time or time period. Since this position of the primary light beam corresponds to the position of the damage, it is thus possible to achieve exact determination of the site of damage.

It is here not necessary (although possible) to explicitly determine or calculate the position of the at least one primary light beam on the phosphor body. Rather, it suffices to correlate the measurement signal with at least one parameter of the light-emitting apparatus from which the position of the at least one primary light beam on the phosphor body can be uniquely derived. Such a parameter can be, for example, a time that has passed since the beginning of an image buildup, a drive voltage of the deflection device, a setting of the deflection device, the length of the track that the at least one primary light beam has traveled on the phosphor body since the beginning of an image buildup, etc.

In one embodiment, step (a) and/or step (b) is followed by triggering of at least one action since in this way in particular a safety function can be implemented by the light-emitting apparatus.

In the simplest case, this action can be a safety switch-off or dimming of the at least one semiconductor light source for emergency light operation.

In another embodiment, the at least one action includes carrying out at least one test illumination of the at least one light-emitting body—e.g. scanning of the entire phosphor area. Due to the test illumination or the test illumination operation, it is possible to check or confirm damage to the phosphor body and/or to more precisely localize the damage. This is useful in particular if the at least one light-emitting body is irradiated by a plurality of primary light beams.

In another embodiment, a test illumination or a test illumination operation can be carried out independently of any damage. This gives the advantage that the phosphor body can be examined for damage in a precautionary fashion. As a result, it is in turn possible to react, for example, to any identified damage before the phosphor body is irradiated for generating used light.

The test illumination can here be triggered or carried out in dependence on an event.

In a further development, the test illumination is, for example, carried out before the light-emitting apparatus is switched on or activated, since the phosphor body can thus be examined preventatively for damage before a used light beam is emitted.

Alternatively or additionally, the test illumination can be carried out before the operating mode is switched from one to another (for example between high beam and fog light), since the phosphor body can thus be examined preventatively for any damage in a region of the phosphor body that was not illuminated in the previously used mode of operation.

In another further development, the test illumination is carried out at specified time intervals or at specified times, since the phosphor body can thus be examined preventatively for any damage before a used light beam is emitted.

In another embodiment, the test illumination can be or is carried out after damage is identified. It is thus possible, for example at an image refresh frequency of 250 Hz, to always use one image buildup per second for the test illumination method. As a result, any occurring damage to the phosphor can be identified in a particularly prompt fashion.

Various types of test illumination can be combined with one another.

In another embodiment, the at least one light-emitting body can be irradiated by at least two disjointed primary light beams and the at least one action includes carrying out a test illumination of the at least one light-emitting body for each individual primary light beam and/or for each individual illumination region. This permits exact localization of the damage on the phosphor body even in the case where, at the time at which the at least one light detector has identified or detected damage, a plurality of disjointed primary light beams has illuminated the phosphor body in the field of vision of a same light detector.

In another embodiment, the at least one action includes subsequent driving of the at least one semiconductor light source and/or of the deflection device such that a region associated with the identified damage ("damage region") on the phosphor body is not illuminated. The damage region is thus excluded from the illumination such that such a light-emitting apparatus ensures both that primary light cannot exit to any damaging degree and that an illumination function can be maintained as far as possible. In the case of only minor damage, it is possible to only limit the illumination function to a practically unnoticeable extent. In vehicles, it is thus possible to significantly increase driving safety.

The damage region can be a damaged region in which damage was identified. The damage region can additionally include a non-damaged region that surrounds the damage, which increases a certainty that the damage is not unintentionally illuminated. In this case, the damage region can thus have a "safety region" or can be referred to as a safety region surrounding the damage.

The damage region that is configured as the safety region can completely surround the damage. In various embodiments, the lateral dimensions thereof can be greater than the respective lateral dimensions of the damage, for example by a fixed ("safety") factor, for example 1.5 or 2. The safety factors for each lateral direction can be fixed individually and, if appropriate, also be changed. The lateral safety factors can thus be changed depending on the operating time of the light-emitting apparatus, e.g. can be increased with increasing operating time. It is also possible to select these safety factors to be larger or smaller depending on a site of damage, i.e. in the center of the phosphor body or of the light-emitting apparatus or at the edge, for example. The form of the damage region can be chosen arbitrarily, for example to be round, elliptic, rectangular, square, polygonal, free-form.

In yet another embodiment, the at least one action includes switching off at least that semiconductor light source by means of which a region on the phosphor body that is associated with the identified damage can be illuminated. This may allow particularly reliable prevention of primary light egressing to a damaging extent. If a plurality of disjointed primary light beams can be generated that illuminate different illumination regions, it can be sufficient to switch off or deactivate only that or those semiconductor light source(s) whose primary light beams would illuminate the damage region. Other semiconductor light sources, however, can be switched on or activated such that the primary light beams thereof continue to illuminate the phosphor body—outside the damage region.

In another embodiment, the identification of damage to the phosphor body is carried out on the basis of a comparison of the at least one measurement signal generated by the at least one light detector with a respective reference signal. Damage can thus be identified or determined with comparatively simple means. The reference signal can have been calculated or measured.

The reference signal is e.g. a signal that is dependent on the position of the at least one primary light beam on the phosphor body. Geometric effects, such as alignments of or distances between components in the light-emitting apparatus (for example from the light detector to the phosphor body) and/or effects with respect to a configuration of the phosphor body, can thus be taken into consideration.

In another embodiment, the measurement signals or the reference signals are normalized with a currently applied light output (for example expressed as the prevailing light source current supply) of the at least one semiconductor light source or of the at least one primary light beam. It is thus possible to also take into consideration for example dimming of the primary light beam and/or pulse modulation of a primary light source and/or saturation of the phosphor, for example triggered by thermal quenching. Modulation of the primary light radiation can advantageously increase the signal-to-noise ratio of the measurement sensors with respect to external interfering variables, for example in the case of sunlight falling into the light-emitting apparatus from the outside.

The reference signals can be normalized in a spatially resolved—for example image-point-wise—fashion, i.e. individual normalization is present or is used or at least an individual normalization value is present or is used, for example, for each image point generated by a primary light beam on the phosphor body. The reference signal can thus be present for example for each spatially resolved point on the phosphor. However, the normalization can also be carried out in a locally averaged fashion, for example averaged by region or row etc.

The reference signal can be derived, for example, from a normalized spatially resolved yellow/blue intensity ratio of a previous test illumination and/or from an average of earlier spatially resolved measurements of the primary light and/or conversion light intensities or the intensity ratios thereof.

The evaluation device can be a dedicated unit or a distributed system. The evaluation device can also carry out other functions, for example driving of the semiconductor light source(s) and/or of the deflection device. The evaluation device can thus be a control device of the light-emitting apparatus which has a corresponding evaluation function.

In another embodiment, the light-emitting apparatus is an illumination apparatus, e.g. a projection apparatus or part of a projection apparatus. Various embodiments are applicable e.g. to projection apparatuses such as vehicle headlights, stage projectors etc.

Various embodiments provide a method which may include, for example, identification of damage to the phosphor body on the basis of at least one measurement signal that is generated by at least one light detector and correlation of the at least one measurement signal with at least one associated setting of the deflection device.

The method may e.g. be an illumination method, in which a phosphor body is illuminated in a scanning fashion using at least one primary light beam, light emitted by the phosphor body is detected, damage to the phosphor body is identified on the basis of the detection, and the identification of the damage is correlated with at least one position on the phosphor body.

Figure 1:
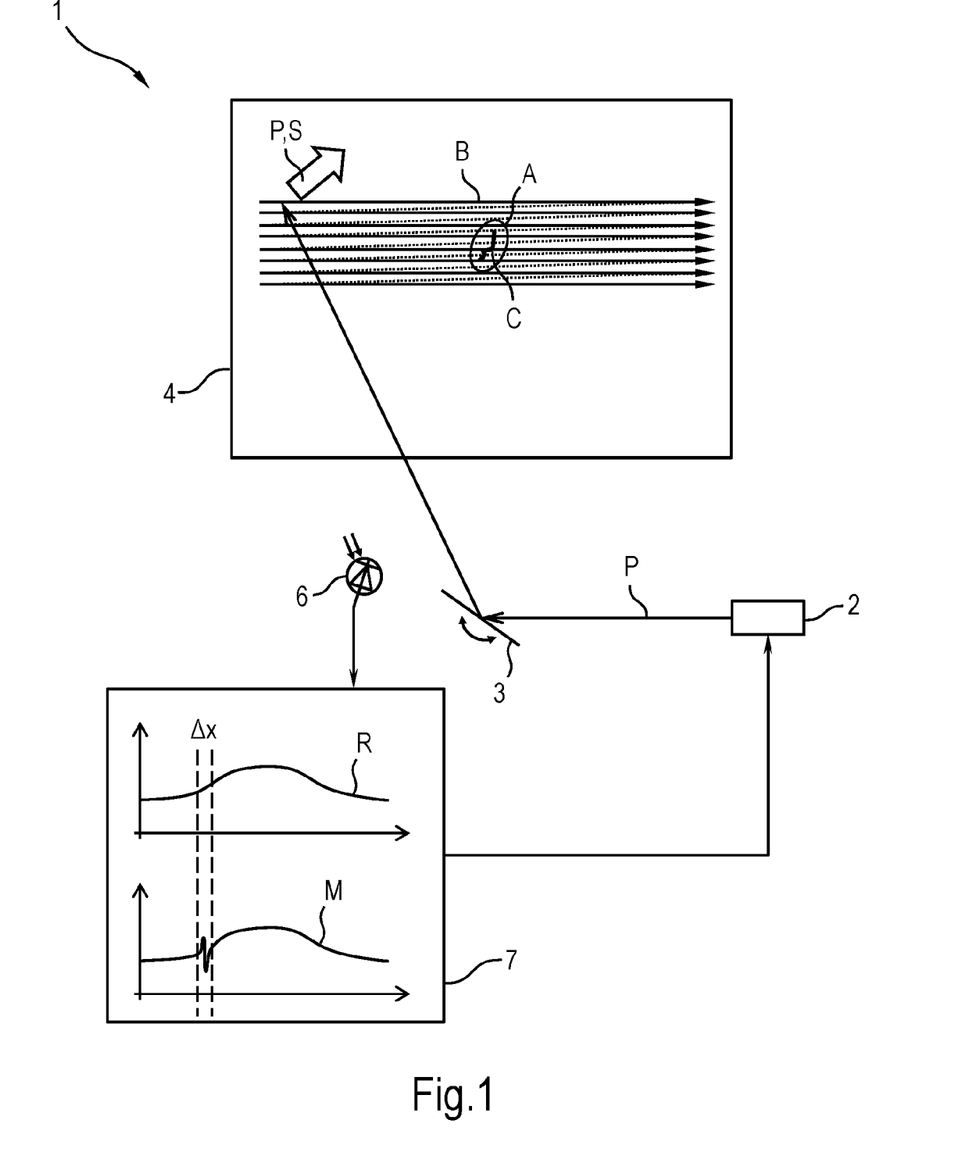
FIG. 1 shows a schematic of a light-emitting apparatus according to a first embodiment.

FIG. 1 shows a schematic of a light-emitting apparatus 1 according to a first embodiment. The light-emitting apparatus 1 has a semiconductor light source in the form of a laser diode 2 which emits a blue primary light beam P. The laser diode 2 can be, for example, an individual laser diode or a group of a plurality of laser diodes, the individual primary light beams of which are combined into a single primary light beam P.

The primary light beam P is deflected by a deflection device having at least one rotatable mirror 3 onto a—e.g. ceramic—plate-shaped phosphor body 4. The at least one mirror 3 is rotatable such that the primary light beam P can define a track B on the phosphor body 4. The track can illuminate the phosphor body 4 in rows or "scan it", as illustrated. To this end, the at least one mirror 3 can assume a plurality of or various angular settings continuously (in particular infinitely variably) so as to deflect the primary light beam P onto different positions on the phosphor body 4 that are associated with the track B.

At the site of the incident primary light beam P, which here creates a light spot, some of the primary light beam P is converted into yellow secondary light S, and the primary light beam P is scattered so that, overall, a yellow-blue or white mixed light P, S is emitted by the phosphor body 4 as the used light at the site of the light spot.

The light-emitting apparatus 1 furthermore has a light detector 6 having, for example, a photodiode which reacts sensitively to the mixed light P, S and can detect both the primary light P and the secondary light S. The field of vision of the light detector 6 includes the entire region of the phosphor body 4 that can be illuminated by the primary light beam P. The light detector 6 is thus configured for detecting the mixed light P, S that was emitted by the phosphor body 4. The light detector 6 may be arranged in the region of the mixed light P, S that is emitted as the used light. In a reflecting arrangement, it faces that side of the phosphor body 4 on which the primary light beam P is also incident. In a transmitting arrangement, the light detector 6 faces that side of the phosphor body 4 that is remote therefrom.

The light-emitting apparatus 1 furthermore has an evaluation device 7 which is configured for (a) identifying damage C of the phosphor body 4 on the basis of at least one measurement signal M that is generated by the light detector 6, and for (b) correlating the at least one measurement signal M with at least one position of the primary light beam P on the phosphor body 4. This is shown in the bottom diagram of the evaluation device 7, while the upper diagram shows a reference signal R. The evaluation device 7 can be a dedicated unit and be coupled, for example, to a control device (not illustrated) for operating the light-emitting apparatus. Alternatively, the evaluation device 7 can be integrated in the control device, for example as a function of the control device.

In both diagrams, the y-axis may indicate a signal parameter of the light detector 6 such as a measurement voltage etc. The x-axis may indicate a parameter that correlates with the position of the primary light beam P on the phosphor body 4, for example a time that has passed since the beginning of an image buildup, a drive voltage of the at least one mirror 3, an angular setting of the at least one mirror 3, a length of the track B that has been traveled since the beginning of an image buildup, etc. The parameter indicated by the x-axis e.g. permits a position of the primary light beam P on the phosphor body 4 to be deduced.

The reference signal R is present e.g. for the duration of an image buildup. It can have been prespecified for a specific type of light-emitting apparatus 1 or determined individually, e.g. measured, for each light-emitting apparatus 1.

For successive measurement points or measurement sections $\Delta x$, the evaluation unit 7 compares the measurement signal M with the corresponding point or section of the reference signal R. If the two signals M and R match with a prespecified accuracy, it is assumed that no damage to the phosphor body 4 exists for this measurement point or measurement section $\Delta x$ (and thus at the associated position on the phosphor body 4). No action is triggered.

The comparison may include normalization or matching of the measurement signal M and/or of the reference signal R to a current electrical and/or light output of the laser diode 2 so as to also be able to take into consideration intended changes in power (for example by dimming the laser diode 2) or unintended changes in power (for example by the effects of temperature and/or aging). To this end, for example, the electric power of the laser diode 2 can be measured.

However, if, as is shown, the measurement signal M (which is normalized, if appropriate) noticeably deviates from the reference signal R, this is interpreted as damage C to the phosphor body 4 at the corresponding point or position. The damage C can for example be a tear, flaking-off, thermal quenching etc. The evaluation unit 7 can, upon identification of the damage C, trigger at least one action that can be dependent on the extent and/or type of the damage C.

In the simplest case, this action may include switching off or dimming the laser diode 2.

One action which maintains the function of the light-emitting apparatus better can be that the evaluation unit 7 determines either the site of the damage C or a damage region A around the damage C, which damage region A is associated with the identified damage C. In the latter case, the damage region A can also be referred to as a "safety region". This determination may include calculation of the position of the damage C or of the associated damage region A on the phosphor body 4, but does not need to. It can be sufficient that corresponding other parameters, which can be correlated uniquely with the position, are determined, for example the time that has passed since the beginning of the image buildup, the drive voltage of the at least one mirror 3, the angular setting of the at least one mirror 3, the length of the track B that has been traveled since the beginning of an image buildup etc.

In the text below, the light-emitting apparatus 1 is operated such that at least every time the primary light beam P were to illuminate the damage C or the associated damage region A, the laser diode 2 does not emit said primary light beam P. This is to say, while the damage C or the associated damage region A is no longer illuminated, the remaining part of the phosphor body 4 can be illuminated as usual. This can significantly increase the functionality of the light-emitting apparatus 1, e.g. if the damage C is only minor.

The damage region A, which is configured as the safety region, can completely surround the damage C. In various embodiments, its lateral dimensions can be greater than the respective lateral dimensions of the damage, for example by a fixed ("safety") factor, for example 1.5 or 2. The safety factors can be individually fixed for each lateral direction and, if appropriate, also be changed. The lateral safety factors can thus be changed depending on the operating time of the light-emitting apparatus 1, e.g. can be increased with increasing operating time. It is also possible to select these safety factors to be larger or smaller depending on a site of damage C, i.e. in the center of the phosphor body 4 or of the light-emitting apparatus 1 or at the edge, for example. The form of the damage region A can be chosen arbitrarily, for example to be round, elliptic, rectangular, square, polygonal, free-form.

As a further action, an alert can be output for example to a monitoring device.

The light-emitting apparatus 1 can also be expanded, for example in a way such that it has a plurality of sets of the components shown in FIG. 1, which can also be operated independently of one another. It is possible here to use a common phosphor body 4. The illumination regions which can be illuminated by the respective primary light beams P can here overlap or be disjointed. Each of the illumination regions can be monitored by at least one respective light detector 6.

The light-emitting apparatus 1 can be a projection apparatus or part of a projection apparatus, for example of a vehicle headlight or an effect or stage projector.

Figure 2:
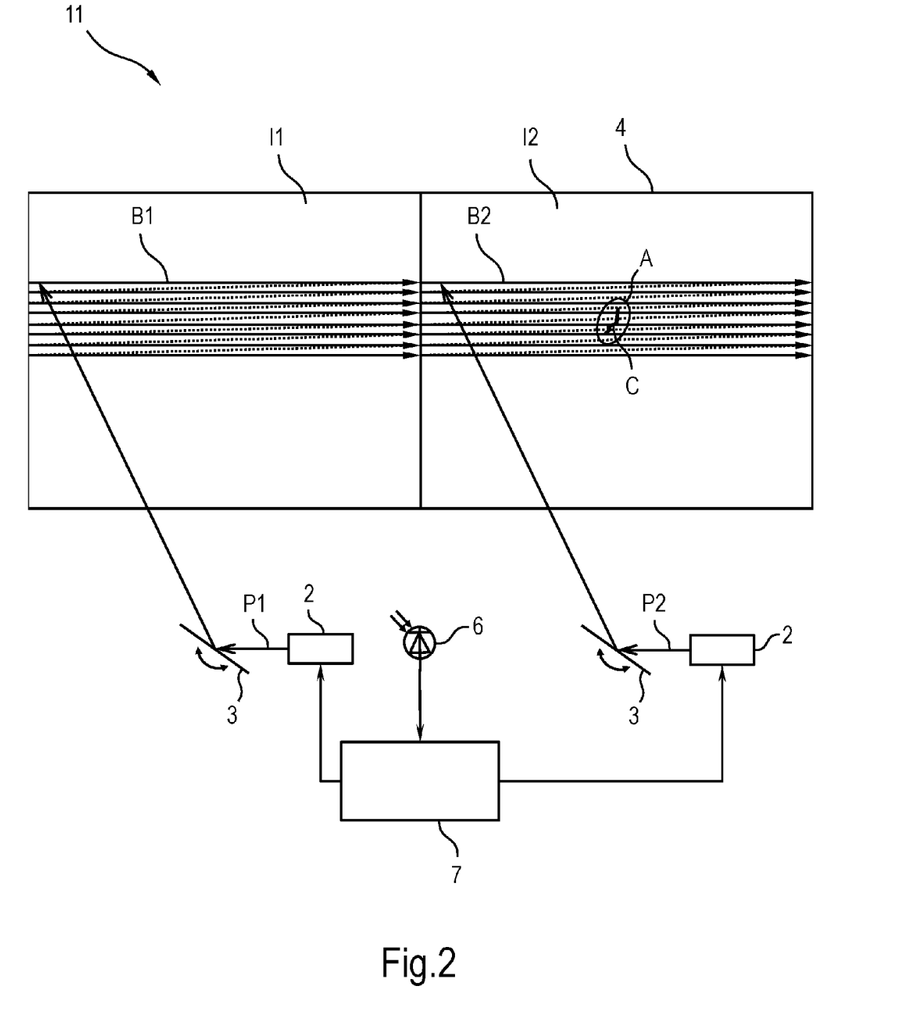
FIG. 2 shows a schematic of a light-emitting apparatus according to a second embodiment.

FIG. 2 shows a diagram of a light-emitting apparatus 11 according to a second embodiment. The light-emitting apparatus 11 differs from the light-emitting apparatus 1 in that the phosphor body 4 can now be illuminated by a plurality of (in the present case, purely by example, two) disjointed primary light beams P1 and P2. The disjointed primary light beams P1 and P2 here illuminate two practically disjointed illumination regions I1 and I2, to which end in each case an arrangement similar to the light-emitting apparatus 1 can be used. The associated tracks B1 and B2 can be the same or different.

Instead of operation which is purely parallel with respect to the light-emitting apparatus 1, the light-emitting apparatus 11 only has at least one light detector 6, which monitors both illumination regions I1 and I2, which can be implemented in a particularly simple and cost-effective manner. The field of vision of the light detector 6 thus includes both illumination regions I1 and I2 and thus in the present case the entire illuminable region of the phosphor body 4. Only one evaluation device 7 is also present.

The evaluation device 7 operates as in the case of the light-emitting apparatus 1. However, it is initially no longer clear in the identification of the damage C in which of the illumination regions I1 and I2 said damage is located. For this reason, upon identification of the damage C, a test illumination is carried out in which the two illumination regions I1 and I2 are illuminated successively in terms of time by their respective primary light beam P1 and P2, e.g. are illuminated completely. The evaluation device 7 can in this way check both illumination regions I1 and I2 individually for damage C. In the case shown, the damage C would be capable of being associated uniquely with the illumination region I2, and actions that are similar to the case of the light-emitting apparatus 1 can be carried out for this illumination region I2. The illumination region I1 can be illuminated independently thereof.

LIST OF REFERENCE SIGNS 1 light-emitting apparatus
2 laser diode
3 mirror
4 phosphor body
6 light detector
7 evaluation device
11 light-emitting apparatus
A damage region
B track on phosphor body
B1 track on phosphor body
B2 track on phosphor body
C damage
$\Delta x$ measurement point or measurement section of the measurement signal
I1 illumination region
I2 illumination region
M measurement signal
P primary light beam
P1 primary light beam
P2 primary light beam
R reference signal
S secondary light Although the invention is further illustrated and described in detail by the illustrated embodiments, the invention is not limited thereto and other variations can be derived therefrom by the person skilled in the art without departing from the scope of protection of the invention.

In general, "a", "an" etc. can be understood to mean the singular or the plural, in particular within the meaning of "at least one" or "at least a" or "one or more" etc., as long as this is not explicitly excluded, for example by the expression "exactly one" etc.

The specification of a number can also include exactly said specified number and also a typical tolerance range, as long as this is not explicitly excluded.

What is claimed is:

1. A light-emitting apparatus, comprising:
   at least one semiconductor light source configured to emit at least one primary light beam;
   a deflection device configured to deflect the at least one primary light beam onto respectively associated different positions on a phosphor body;
   at least one light detector configured to detect light that was emitted by the phosphor body; and an evaluation device configured to:
- identify damage to the phosphor body on the basis of at least one measurement signal generated by the at least one light detector;
- correlate the at least one measurement signal with at least one position on the phosphor body.

2. The light-emitting apparatus of claim 1, wherein identifying damage to the phosphor body on the basis of at least one measurement signal generated by the at least one light detector is followed by triggering of at least one action.

3. The light-emitting apparatus of claim 2, wherein the at least one action comprises carrying out at least one test illumination of the at least one phosphor body.

4. The light-emitting apparatus of claim 3, wherein the at least one phosphor body can be irradiated by at least two disjointed primary light beams and the at least one action comprises carrying out a test illumination of the at least one phosphor body for each individual primary light beam.

5. The light-emitting apparatus of claim 3, wherein the light-emitting apparatus is configured to carry out the test illumination after identification of any damage.

6. The light-emitting apparatus of claim 3, wherein the light-emitting apparatus is configured to carry out the test illumination independently of any damage.

7. The light-emitting apparatus of claim 1, wherein correlating the at least one measurement signal with at least one position on the phosphor body is followed by triggering of at least one action.

8. The light-emitting apparatus of claim 7, wherein the at least one action comprises carrying out at least one test illumination of the at least one phosphor body.

9. The light-emitting apparatus of claim 8, wherein the at least one phosphor body can be irradiated by at least two disjointed primary light beams and the at least one action comprises carrying out a test illumination of the at least one phosphor body for each individual primary light beam.

10. The light-emitting apparatus of claim 8, wherein the light-emitting apparatus is configured to carry out the test illumination after identification of any damage.

11. The light-emitting apparatus of claim 8, wherein the light-emitting apparatus is configured to carry out the test illumination independently of any damage.

12. The light-emitting apparatus of claim 1, wherein the at least one action comprises at least one of subsequent driving of the at least one semiconductor light source or subsequent driving of the deflection device such that a damage region associated with the identified damage on the phosphor body is not illuminated.

13. The light-emitting apparatus of claim 1, wherein the at least one action comprises switching off at least that semiconductor light source by means of which a region on the phosphor body that is associated with the identified damage can be illuminated.

14. The light-emitting apparatus of claim 1, wherein the entire illuminable region of the phosphor body can be monitored by a light detector.

15. The light-emitting apparatus of claim 1, wherein the identification of damage to the phosphor body is carried out on the basis of a comparison of the at least one measurement signal generated by the at least one light detector with a respective reference signal.

16. The light-emitting apparatus of claim 15, wherein the measurement signals or the reference signals are normalized with a currently applied light output.

17. The light-emitting apparatus of claim 1, wherein the light-emitting apparatus is a projection apparatus or part of a projection apparatus.

18. An illumination method, comprising:
- illuminating a phosphor body in a scanning fashion using at least one primary light beam;
- detecting light emitted by the phosphor body;
- identifying damage to the phosphor body on the basis of the detection; and
- correlating the identification of the damage with at least one position on the phosphor body.

* * * * *